(12) United States Patent
Robertson

(10) Patent No.: US 11,869,676 B1
(45) Date of Patent: Jan. 9, 2024

(54) INTERDISCIPLINARY HEALTH AND WELLNESS SYSTEM AND METHOD OF USE

(71) Applicant: Chiquita Robertson, Denham Springs, LA (US)

(72) Inventor: Chiquita Robertson, Denham Springs, LA (US)

( * ) Notice: Subject to any disclaimer, the term of this patent is extended or adjusted under 35 U.S.C. 154(b) by 176 days.

(21) Appl. No.: 17/307,864

(22) Filed: May 4, 2021

(51) Int. Cl.
*G16H 80/00* (2018.01)
*G16H 20/60* (2018.01)
*G16H 20/30* (2018.01)

(52) U.S. Cl.
CPC .............. *G16H 80/00* (2018.01); *G16H 20/30* (2018.01); *G16H 20/60* (2018.01)

(58) Field of Classification Search
CPC ......... G16H 80/00; G16H 20/30; G16H 20/60
USPC ...................................................... 340/573.1
See application file for complete search history.

(56) References Cited

U.S. PATENT DOCUMENTS

| | | | |
|---|---|---|---|
| 8,690,578 B1* | 4/2014 | Nusbaum | G16Z 99/00 705/2 |
| 2017/0235909 A1* | 8/2017 | Lozano | G16H 40/20 705/3 |
| 2019/0159720 A1* | 5/2019 | Geronimo-Button | A61B 5/4842 |
| 2019/0333613 A1* | 10/2019 | Zaidi | G16H 40/63 |
| 2021/0090741 A1* | 3/2021 | Thierry | H04W 4/029 |

\* cited by examiner

*Primary Examiner* — Naomi J Small
(74) *Attorney, Agent, or Firm* — AVEK IP, LLC

(57) ABSTRACT

An interdisciplinary health and wellness system for providing multiple disciplinaries on a single platform to develop a personalized interdisciplinary regimen for improving a user's health and wellness is disclosed. The user interacts with a user interface via a computing device to access information. A specialist may communicate with the user through a specialist interface via a computing device.

3 Claims, 3 Drawing Sheets

INTERDISCIPLINARY HEALTH AND WELLNESS SYSTEM AND METHOD OF USE

BACKGROUND

1. Field of the Invention

The present invention relates generally to health and wellness systems, and more specifically to an interdisciplinary health and wellness system for providing a user a means to access dietary, medical, and physical fitness specialists, tools, resources, and the like for improved overall health and wellness.

2. Description of Related Art

Health and wellness systems are well known in the art and are effective means for providing encouragement and counsel to individuals seeking improvements in their overall health and wellness. However, health and wellness systems are expensive and can be challenging for many individuals to obtain access to needed services. For example, an individual's overall health and wellness is dependent on a number of factors such as medical history, fitness activity, nutrition, genetics, emotional states, and the like. Each factor can fall under separate disciplinaries, and individuals seeking counsel may need to see separate specialists to address each individual factor. Even if an individual obtains access to separate specialists, it takes considerable time and effort for the individual to understand the interrelationships between all of these factors and how they may be utilized in optimizing the individual's overall health and wellness. This can be discouraging and can lead to individuals foregoing needed services.

Hence, it would be advantageous to have a system that provides multiple healthcare disciplines for users and facilitates the creation of interdisciplinary regimens at reduced costs, thereby encouraging users to improve their overall health and wellness.

Accordingly, although great strides have been made in the area of health and wellness systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
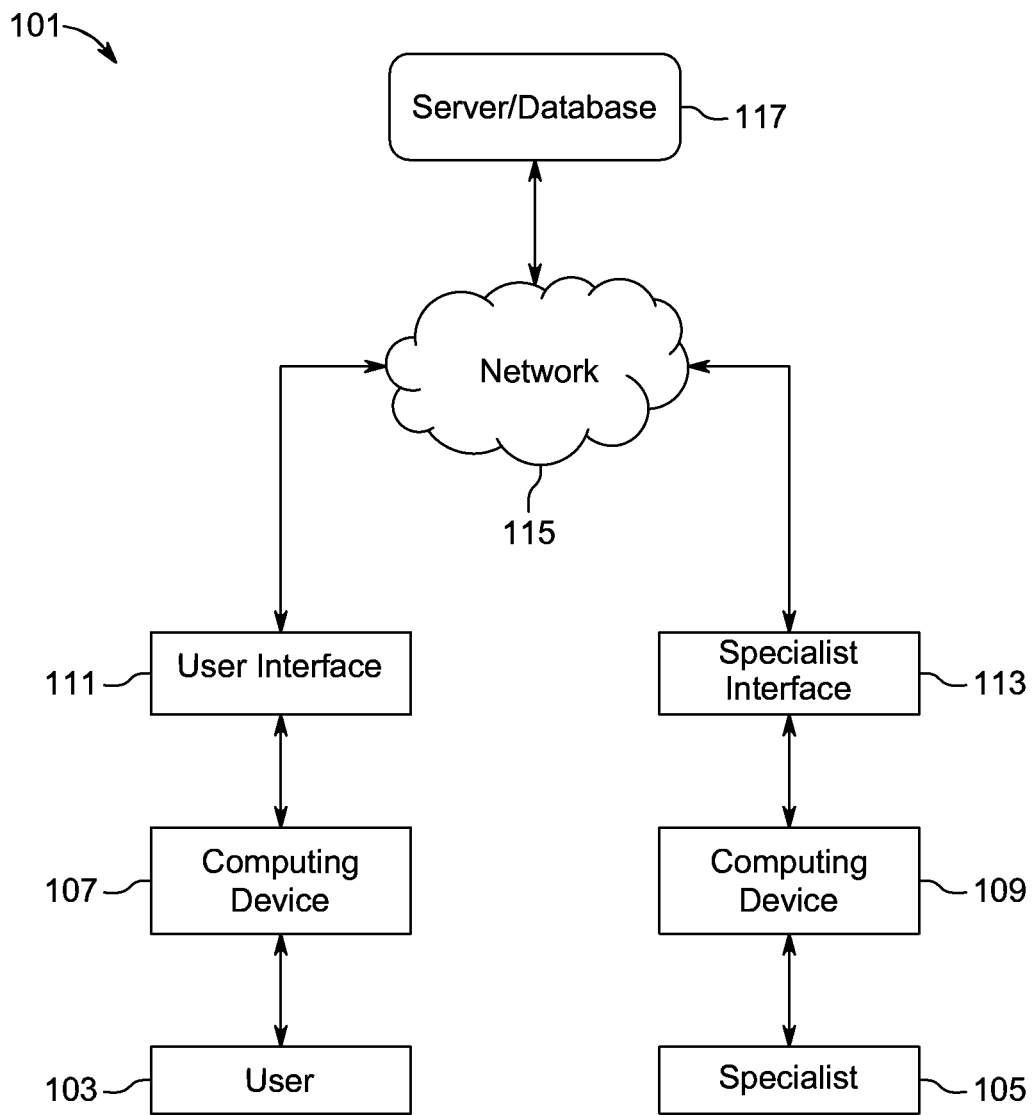
FIG. 1. is a schematic of an interdisciplinary health and wellness system in accordance with a preferred embodiment of the present invention.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional health and wellness systems. Specifically, the present invention provides a means for a user to access services from multiple disciplinaries via a user interface. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Note that throughout the following discussion, numerous references may be made regarding servers, services, engines, modules, interfaces, portals, platforms, or other systems formed from computing devices. It should be appreciated that the use of such terms is deemed to represent one or more computing devices having at least one processor configured to or programmed to execute software instructions stored on a computer readable tangible, non-transitory medium or also referred to as a processor-readable medium. For example, a server can include one or more computers operating as a web server, database server, or other type of computer server in a manner to fulfill described roles, responsibilities, or functions. Within the context of this document, the disclosed devices or systems are also deemed to comprise computing devices having a processor and a non-transitory memory storing instructions executable by the processor that cause the device to control, manage, or otherwise manipulate the features of the devices or systems.

Embodiments may comprise a computer program that embodies the functions described and illustrated herein, wherein the computer program is implemented in a computer system that comprises instructions stored in a machine-readable medium and a processor that executes the instructions. It should be appreciated that there may be many different ways of implementing embodiments in computer programming and the embodiments should not be construed as limited to any one set or computer program instructions. Further, a skilled programmer would be able to write such a computer program to implement an embodiment of the disclosed embodiments based on the appended flowcharts and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described herein. The systems, methods and procedures described herein can be embodied in a programmable computer, computer-executable software, or digital circuitry. The software can be stored on computer-readable media, for example, read-only memories (ROMs), random access memories (RAMs), hard disks, floppy disks, compact disk read only memory (CD-ROM), optical disks, magneto-optical media, etc. Digital circuitry can include integrated circuits, gate arrays, building block logic, field programmable gate arrays (FPGA), etc.

Referring now to the drawings wherein like reference characters identify corresponding or similar elements throughout the several views, FIG. 1 depicts a schematic of an interdisciplinary health and wellness system 101 in accordance with a preferred embodiment of the present application. It will be appreciated that the interdisciplinary health and wellness system 101 overcomes one or more of the above-listed problems commonly associated with conventional health and wellness systems.

In the contemplated embodiment, the interdisciplinary health and wellness system 101 allows for communication among a user 103 and a specialist 105. The user 103 engages with a computing device 107 to interact with a user interface 111 to facilitate communication via a network 115. The specialist 105 engages with a computing device 109 to interact with a specialist interface 113 to facilitate communication via the network 115.

The user 103 includes one or more individuals interacting within the interdisciplinary health and wellness system 101. It should be appreciated that the user 103 may include prospective clients, clients, other clients, or any combination or multiplicity thereof interacting within the interdisciplinary health and wellness system 101.

The specialist 105 is an individual who specializes in a particular healthcare discipline and provides counsel based on the particular field to the user. It should be appreciated that the specialist 105 may include one or more physicians, physical therapists, psychologists, nutritionists, dieticians, other healthcare provider, or any combination or multiplicity thereof interacting within the interdisciplinary health and wellness system 101. In addition, it should be appreciated that the specialist 105 may be tools, resources, and other materials that provide information for improved overall health and wellness. For example, the tools, resources, and other materials may provide information pertaining to meal plans, exercise programs, sleep programs, mental health exercises, and the like.

The computing devices 107, 109 may correspond to one or more personal computers, laptop computers, personal digital assistants, tablet computers, mobile phones, portable media players, digital media receivers, set-top boxes, kiosks, video game consoles, printers, scanners, any other network-enabled electronic devices, or any combination or multiplicity thereof.

The user interface 111 and the specialist interface 113 may be incorporated into any type of software application, including, without limitation, desktop applications, mobile applications, and web-based applications to enable users to interact with and control the applications. In addition, the user interface 111 and the specialist interface 113 may access a server/database 117 via the network 115 using a software application, a browser application, a web browser, a webpage, a website, or any combination or multiplicity thereof.

In some embodiments, the user interface 111 may prompt the user 103 to create a user profile which may include the health and wellness information about the user 103, the history of the user 103 interacting within the interdisciplinary health and wellness system 101, overall summary of the interdisciplinary regimen provided by the specialist 105, and the like.

In other embodiments, the user interface 111 may prompt the user 103 to complete an information form, survey, questionnaire, any other information gathering method, or a combination or multiplicity thereof.

The network 115 includes one or more wired telecommunications, wireless telecommunications, or any combination or multiplicity thereof by which the computing devices 107, 109 may exchange data. The network may include, for example, one or more of a local area network (LAN), a wide area network (WAN), an intranet, an Internet, a public switched telephone network (PSTN), a metropolitan area network (MAN), a cellular or other mobile communication network, a BLUETOOTH® wireless technology connection, a wireless local area network (WLAN), a virtual private network (VPN) a near field communication (NFC) connection, and any combination or multiplicity thereof.

The server/database 117 is configured to manage network resources, store information, data processing, and the like needed to implement the methodologies discussed herein. It should be appreciated that the server/database 117 includes one or more servers, for example, a web server, an application server, a database server, and any combination or multiplicity thereof to apply the current invention. In addition, it should be appreciated that the server/database 117 includes one or more databases, for example, a structural query language (SQL) databases or other relational database, a flat or hierarchical structure of files, a single flat-file store, a key-value mapping system, or other forms of data storage known to those of ordinary skill in the art.

The server/database 117 may also be configured to store, retrieve, and send computer files and data to other computing devices on network 115. The server/database 117 may also be configured to control the storage, organization, and retrieval of data and information. For example, in some embodiments, data and information may include information pertaining to the user 103, the specialist 105, healthcare, meal plans, exercise programs, sleep programs, mental health exercises, and the like. In other embodiments, the server/database 117 may delegate certain data and information only available to the user 103, the specialist 105, or shared between the user 103 and the specialist 105. In some embodiments, the server/database 117 may withhold certain data and information from the user 103 if the user 103 is a prospective client.

It should be appreciated that during use, when the user 103 seeks healthcare services from different healthcare disciplines, the user 103 is connected to the appropriate specialists in real-time or at a scheduled time. The user 103 is then connected to other specialists to receive the remaining healthcare services.

It should also be appreciated that one of the unique features believed characteristic of the present application is that it reduces costs associated with healthcare services by providing users access to specialists from multiple healthcare disciplines, thereby allowing users to improve their overall health and wellness.

Figure 2:
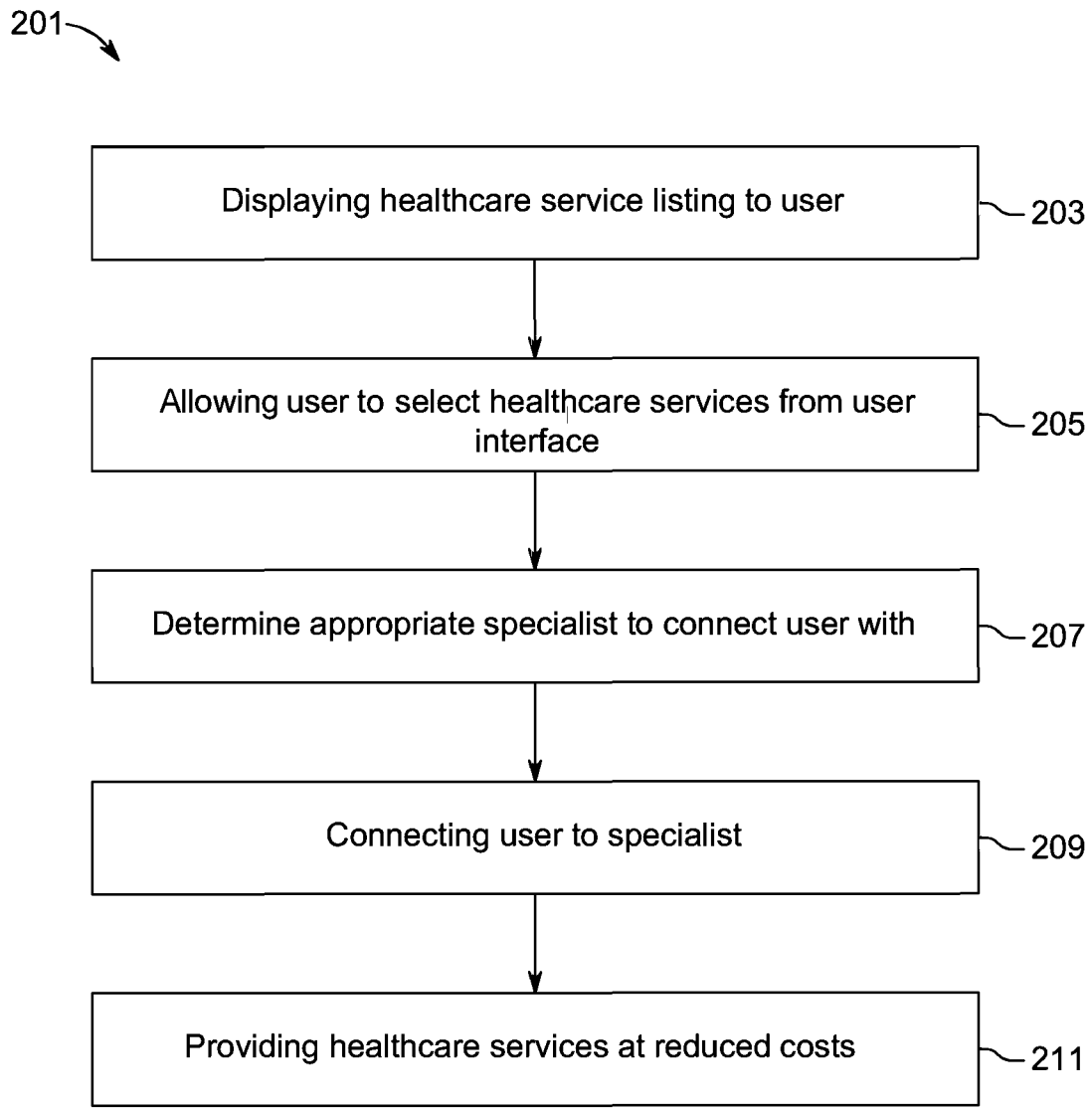
FIG. 2 is a flowchart of a method of operation of the interdisciplinary health and wellness system of FIG. 1.

In FIG. 2, a flowchart 201 depicts a method of operation associated with the present invention. During operation, a listing of one or more healthcare services is displayed to the user via the user interface, as shown with box 203. The listing of one or more healthcare services may include healthcare, meal plans, exercise programs, sleep programs, mental health exercises, and the like.

The user may then select one or more healthcare services from the user interface, as shown with box 205. When the appropriate specialist is determined, the appropriate specialist is connected to the user via the specialist interface, as shown with boxes 207, 209.

Healthcare services are then provided to the user at reduced costs, as shown with box 211. The healthcare services rendered may include prescriptions, meal plans, mental health counseling and the like. In addition, the healthcare services may be provided in real-time, at a scheduled time, or a time convenient for the user. Further, the healthcare services may be provided to the user without needing to connect with a specialist.

Figure 3:
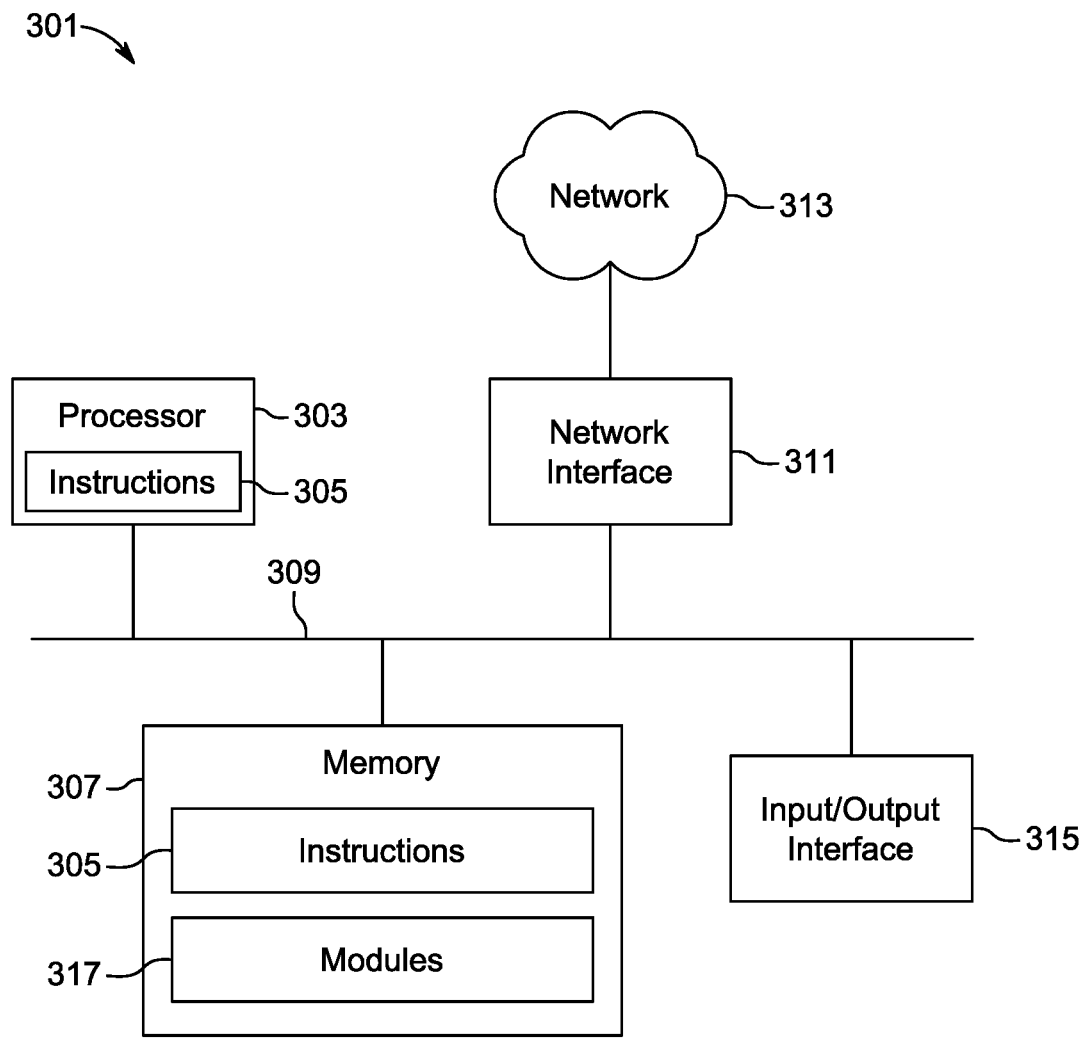
FIG. 3 is a block diagram illustrating an example computer system in the example form of a machine within which a set of instructions for causing the machine to perform any one or more of the methodologies discussed herein may be executed.

Referring now to FIG. 3, a block diagram of a machine in the example form of a computer system 301 within which a set of instructions for causing the machine to perform any one or more of the methodologies discussed herein, may be executed. The computer system 301 may correspond to any of the various computing devices, servers, mobile devices, embedded systems, or computing systems presented herein.

The computer system 301 may be implemented as any of a variety of conventional computing devices, including, for example, a desktop computer, a laptop, a tablet, a phablet, a workstation, an embedded controller, a server, a mobile device, a smartphone, an entertainment device, a printing machine (also referred as a printer or a printing device), a set-top box, a kiosk, a vehicular information system, one or more processors associated with a television, a customized machine, any other hardware platform, or any combination or multiplicity thereof. The computer system 301 may be a distributed system configured to function using multiple computing machines interconnected via a data network or bus system. Further, while only a single machine is illustrated, the term "machine" shall also be taken to include any collection of machines that individually or jointly execute a set (or multiple sets) of instructions to perform any one or more of the methodologies discussed herein.

The computer system 301 includes at least one processor 303 with or without one or more sets of instructions 305, a memory 307 with or without one or more sets of instructions 305, a network interface 311, and an input/output interface 315 which communicate with each other via a bus 309.

The processor 303 may be configured to execute code or instructions to perform the operations and functionality described herein, manage request flow and address mappings, and to perform calculations and generate commands. The processor 303 may be configured to monitor and control the operation of the components in the computer system 301. The processor 303 may be a general purpose processor, a processor core, a multiprocessor, a reconfigurable processor, a microcontroller, a digital processor (DSP), an application specific integrated circuit (ASIC), a graphics processing unit (GPU), a field programmable gate array (FPGA), a programmable logic device (PLD), a controller, a state machine, grated logic, discrete hardware components, any other processing unit, or any combination or multiplicity thereof. The processor 303 may be a single processing unit, multiple processing cores, special purpose processing cores, co-processors, or any combination thereof. In addition, the processor 303 along with other components of the computer system 301 may be a virtualized computing machine executing within one or more other computing machines.

The processor 303 may also be connected to the other elements of the computer system 301 or the various peripherals discussed herein through the bus 309. It should be appreciated that the bus 309 may be within the processor 303, outside the processor 303, or both. In some embodiments, any of the processor 303, the other elements of the computer system 301, or the various peripherals discussed herein may be integrated into a single device, for example, a system on a chip (SOC), system on package (SOP), or application-specific integrated circuit (ASIC) device.

The instructions 305 may reside, completely or at least partially, within the processor 303 and/or memory 307 during execution thereof by the computer system 301. The instructions 305 may include directions for storing instructions, performing one or more functions, and the like. For example, the instructions 305 may include detecting one or more files to perform one or more methodologies described herein. The instructions 305 may be configured to run in sequential order, in parallel (such as under different processing threads) or in a combination thereof. The instructions 305 may further be transmitted or received over the network 313 using a transmission medium, for instance network interface 311, and any one of a number of well-known transfer protocols (e.g., HTTP, HTTPS, FTP, TCP, and the like).

The network interface 311 facilitates communication with other computing systems (not shown) via one or more networks 313. Other computing systems, for example, may include conventional computing devices as described above, internet connected devices/systems, or an external storage such as a server, or a cloud computing system.

The computer system 301 may operate in a networked environment using logical connections through the network interface 311 to one or more other systems or computing machines across the network 313. The network 313 may include wide area networks (WAN), local area networks (LAN), the Internet, intranets, wireless access networks, wired networks, mobile networks, telephone networks, near field communication (NFC), optical networks, or combinations thereof. The network 313 may be packet switched, circuit switched, of any topology, and may use any communication protocol. Communication links within the network 313 may involve various digital or analog communication media, for example, fiber optic cables, free-space optics, waveguides, electrical conductors, wireless links, antennas, radio frequency communications, and the like.

The memory 307 may include volatile memories, for example, random access memory (RAM), static random access memory (SRAM), dynamic random access memory (DRAM), and synchronous dynamic random access memory (SDRAM). Other types of RAM also may be used to implement the memory 307. The memory 307 may also include non-volatile memories, for example, read-only memory (ROM), erasable programmable read-only (EROM), flash memories, or any other device capable of storing program instructions or data with or without applied power. In addition, the memory 307 may include a non-volatile storage device, for example, a hard disk, a floppy disk, an optical disk, a compact disk read only memory (CD-ROM), a digital versatile disc (DVD), a Blu-ray disc, a magnetic tape, a flash memory, other non-volatile memory device, a solid state drive (SSD), any magnetic storage device, any optical storage device, any semiconductor storage device, any physical-based storage device, any other data storage device, or any combination or multiplicity thereof.

The memory 307 may also include one or more modules 317 configured to facilitate the computer system 301 with performing the methodologies described herein. The module 317 may include one or more sets of instructions 305 stored as software or firmware in association with the memory 307. The memory 307 may therefore represent examples of machine or computer readable media on which instructions or code may be stored for execution by the processor 303. Machine or computer readable media may generally refer to any medium or media used to provide instructions to the processor 303. Such machine or computer readable media associated with the module 317 may comprise a computer software product. It should be appreciated that a computer software product comprising the module 317 may also be associated with one or more processes or methods for delivering the module 317 to the computer system 301 via the network 313, any signal-bearing medium, or any other communication or delivery technology. The module 317 may also comprise hardware circuits or information for configuring hardware circuits, for example, microcode or configuration information for a FPGA or other PLD.

The input/output (I/O) 315 may couple the computer system 301 to various input devices including keyboards, mice, touchscreens, touchpads, trackballs, joysticks, cameras, microphones, scanners, electronic digitizers, sensors, receivers, wireless remotes, and any other pointing devices, or any combination thereof. The I/O 315 may couple the computer system 301 to various output devices including video displays, speakers, printers, projectors, tactile feedback devices, automation control, robotic components, actuators, motors, fans, solenoids, valves, pumps, transmitters, signal emitters, lights, and the like.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An interdisciplinary health and wellness system, comprising:
   a computer system, the computer system having:
      one or more communication interfaces, the interfaces including an input device and a display device;
      one or more communication components receiving data and information via one or more networks;
      one or more processors for executing computer-executable instructions; and
      one or more memories for storing computer-executable instructions that when executed by the one or more processors cause the computer system to perform steps comprising:
         providing a user interface on a computing device, the user interface prompts a user for information related to the user's health and wellness;
         displaying a listing of a plurality of health and wellness services to the user through the user interface, wherein the listing is based, at least in part, on the information related to the user's health and wellness, wherein the listing of the plurality of health and wellness services include dietary, medical, and physical fitness services;
         connecting the user, through the computing device and the user interface, to a plurality of health and wellness specialists through a network, the plurality of health and wellness specialists are a group of health and wellness specialists with at least one specialists from each of a plurality of fields, the plurality of fields including physicians, physical therapists, psychologists, nutritionists, and dieticians;
         matching one of the plurality of health and wellness specialists with the user based at least in part on the information provided by the user;
         providing a specialist interface configured to render on a second computing device, configured to facilitate communication between a matched specialist of the plurality of health and wellness specialists and the user;
         receiving input data indicative of the user selecting one or more of the health and wellness services;
         connecting the user with the matched specialist, wherein the connection of the user with the matched specialist is based, at least in part, on the one or more health and wellness services selected by the user; and
         allowing the matched specialist to communicate directly with the user via the display device.

2. The system of claim 1, wherein the information related to the user's health and wellness further comprises a plurality of factors including a user's medical history, a user's fitness activity, a user's nutrition, a user's genetics, and a user's emotional state.

3. The system of claim 1, wherein the steps further comprise connecting the user to a second of the plurality of health and wellness specialists through the user interface, the second of the plurality of health and wellness specialists being in a different field of the plurality of fields from the matched specialist.

* * * * *